United States Patent [19]

Iizuka et al.

[11] 4,281,021
[45] Jul. 28, 1981

[54] METHOD OF ACCELERATING COLORING AND SWEETENING OF CITRUS FRUITS

[75] Inventors: Chiyokichi Iizuka; Hiroaki Maeda, both of Chiba, Japan

[73] Assignee: Noda Shokkin Kogyo Kabushiki Gaisha, Noda, Japan

[21] Appl. No.: 66,837

[22] Filed: Aug. 15, 1979

[30] Foreign Application Priority Data

May 10, 1979 [JP] Japan .................................. 54/57367

[51] Int. Cl.³ ............................................. A23L 1/272
[52] U.S. Cl. ...................................... 426/61; 426/262; 426/302; 426/102; 426/616
[58] Field of Search ............... 426/102, 262, 270, 616, 426/431, 533, 540, 655, 302, 61, 310

[56] References Cited

U.S. PATENT DOCUMENTS

| | | | |
|---|---|---|---|
| 3,833,350 | 9/1974 | Cooke et al. | 426/270 |
| 3,911,153 | 10/1975 | Yokoyama et al. | 426/616 |
| 3,924,010 | 12/1975 | Erb | 426/270 |

FOREIGN PATENT DOCUMENTS

| | | | |
|---|---|---|---|
| 47-18657 | 9/1972 | Japan | 426/270 |
| 51-82753 | 7/1976 | Japan | 426/270 |

*Primary Examiner*—Jeanette M. Hunter
*Attorney, Agent, or Firm*—Haseltine and Lake

[57] ABSTRACT

This is a method in which a liquid extract containing effective ingredients is obtained from water solutions of Mycelium nutrient medium and tissue-medium from edible fungus belonging to the genus Basidiomycetes and is diluted with water and sprayed over the surface of the leaves to accelerate coloring and improve sweetness of citrus fruits.

4 Claims, 14 Drawing Figures

● Treated Section  ○ Untreated Section

Secular changes in pigment
in the pericarp of Sweetish Summer Oranges 445 mµ Yellow pigment
660 mµ Green pigment

•————• Treated Section   ◦————◦ Untreated Section

Secular changes in pigment
in the pericarp of Sweetish Summer Oranges 445 mµ Yellow pigment
660 mµ green pigment

•———• Treated Section    ○———○ Untreated Section

Secular changes in the pigment in the pericarp of Mandarin Oranges

445mμ Yellow pigment
660mμ green pigment

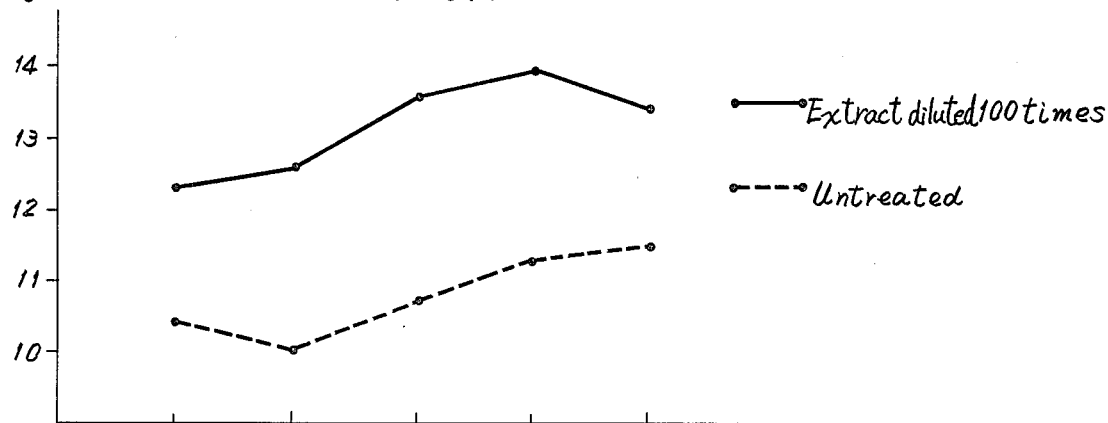
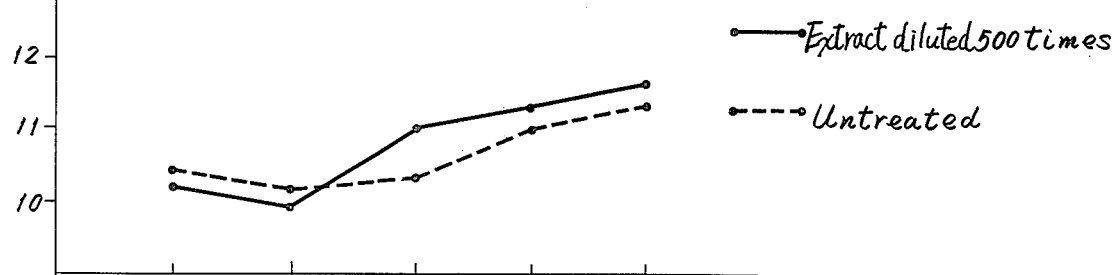
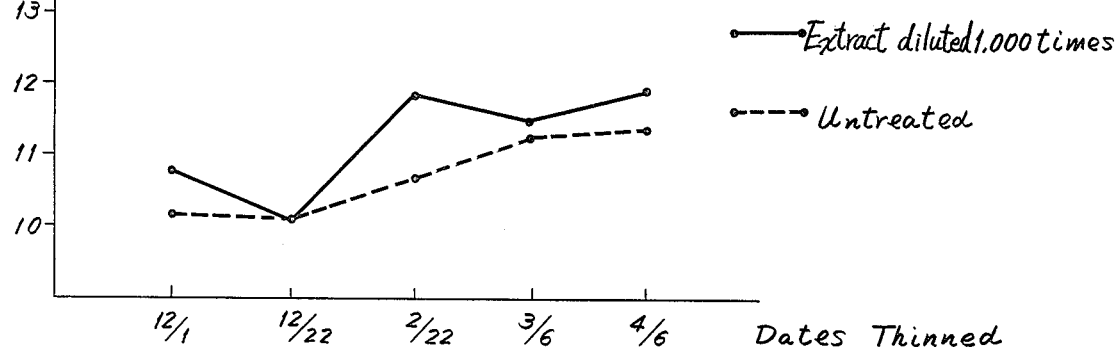
Comparison (Sugar) of Mandarin Oranges in treated and Untreated Sections

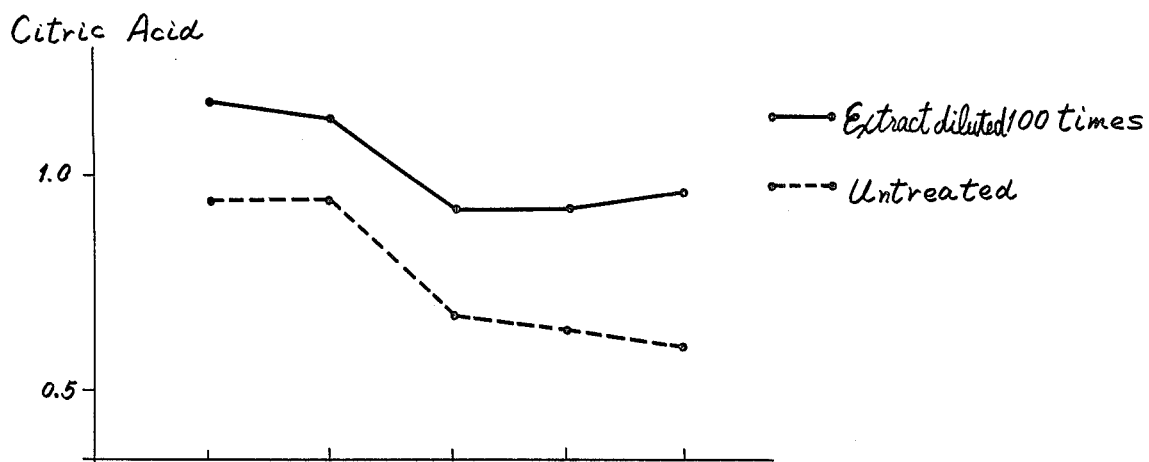
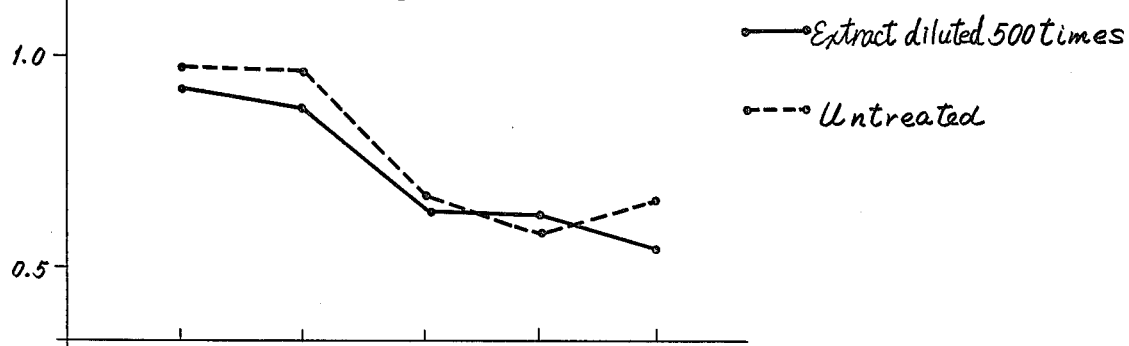
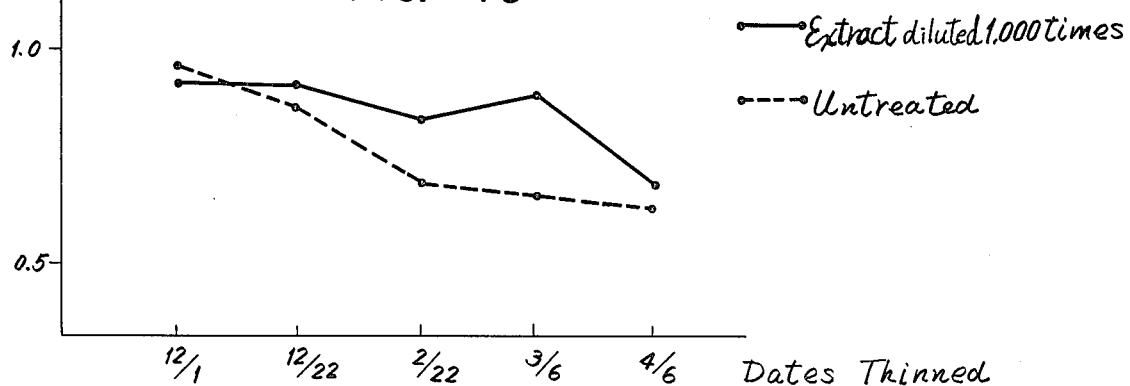
Comparison (Citric Acid) Mandarin Oranges in treated sections and Untreated Section Secular changes of the pigment in the pericarp of Mandarin Oranges 445 mμ Yellow pigment
660 mμ Green pigment

•———• Treated Section  ○———○ Untreated Section

Secular changes of the pigment in the pericarp of Mandarin Oranges 445 mμ Yellow pigment
660 mμ Green pigment dimensional 4,281,021

METHOD OF ACCELERATING COLORING AND SWEETENING OF CITRUS FRUITS

BACKGROUND OF THE INVENTION

This is an invention to accelerate coloring and improve sweetness of citrus fruits by obtaining extracts containing effective ingredients from water solutions of mycelium nutrient medium and tissue-medium of edible fungus belonging to the genus Basidiomycetes and, after diluting with water, spraying this over the surface of the leaves to accelerate coloring and increasing sugar content. As accelerating coloring of citrus fruits is carried out with the prerequisite or early shipment, which will be advantageous in marketing, it is an important facet in the cultivation of citrus fruits. Not only does it also improve the quality from the standpoint of taste and sweetness, it is also an important process from the viewpoint of preventing deterioration in quality. In the past, several types of chemicals were developed for this purpose. For instance, ethylene was used to accelerate coloring. However, in addition to infuring the tree and increasing defoliation, problems were also involved in relation to safety. There were also examples of sulfur being employed as a sweetening agent but again there were problems in relation to safety and its detrimental effect on the tree. This method is therefore not in general use. In addition, chemicals capable of accelerating coloring and improving sweetness at the same time have yet to be developed. However, as a result of various research projects carried out over many years in relation to mecelium of edible fungus belonging to the genus Basidiomydetes by the inventor, numerous inventions were made in relation to methods of extracting chemical ingredients contained in the mycelium. On one hand, it was discovered that the extract of mycelium nutrient medium and tissue-medium contained a substance having cytokinin activity. This invention was made when the extract was sprayed over the citrus fruits as in the foregoing and it was accidentally discovered that it was extremely effective in accelerating coloring and increasing sweetness.

SUMMARY OF THE INVENTION

The principal purpose of this invention is to offer a method of accelerating coloring and increasing sweetness with superior safety characteristics that means toxicity (L.D. 50) of extract dry matter is Rat ♂ 16.5 g, ♀ 15.6 g, Mouse ♂ 19.6 g, ♀ 17.7 g per kg. (body weight) and, moreover, a method that will not detrimentally affect the tree in any way.

Another purpose of this invention is to offer a low cost method of accelerating coloring and increasing sweetness which would be capable of attaining these two purposes simultaneously. A further purpose of this invention is to make possible early harvesting of citrus fruits and, moreover, enable growing citrus fruits of superior quality.

In the figures, 445 m$\mu$ indicates yellowish pigment and 660 m$\mu$ greenish pigment.

Figure 2A:
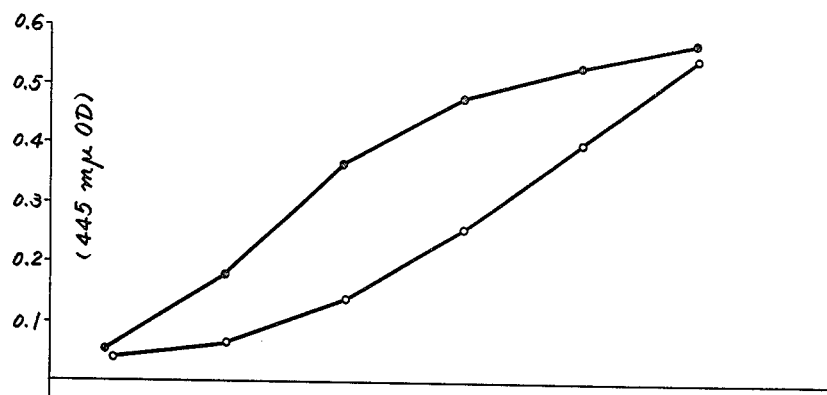
Figure 2B:
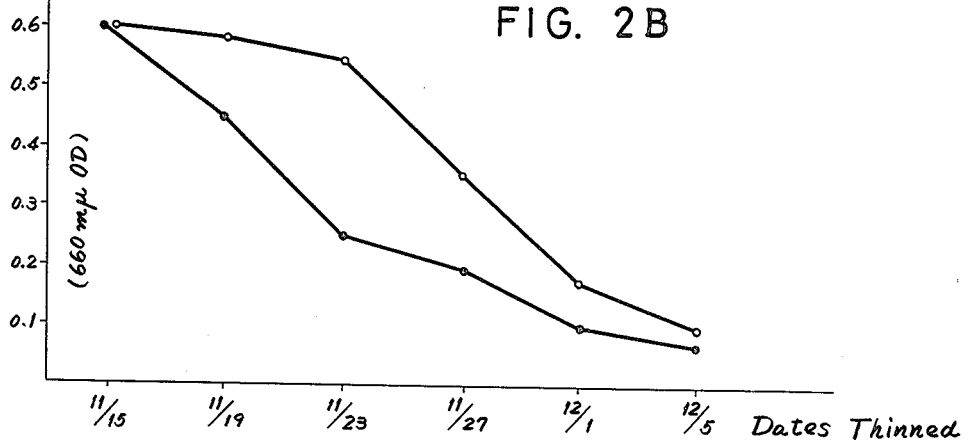

FIGS. 2A and 2B are graphs showing secular changes of the pigment in the pericarp of mandarin oranges in experiment 2.

FIGS. 3A to 3C and 4A to 4C are graphs showing comparisons between this fluid extract undiluted and diluted 100 times particularly in relation to sugar and citric acid content of the analysis results in experiment 3.

Drawings 5A and 5B are graphs showing secular changes of the pigment in the pericarp of sweetish summer oranges in experiment 4.

Figure 6A:
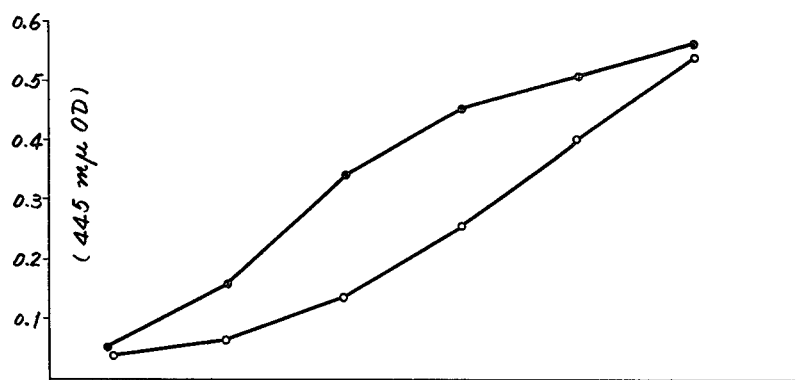
Figure 6B:
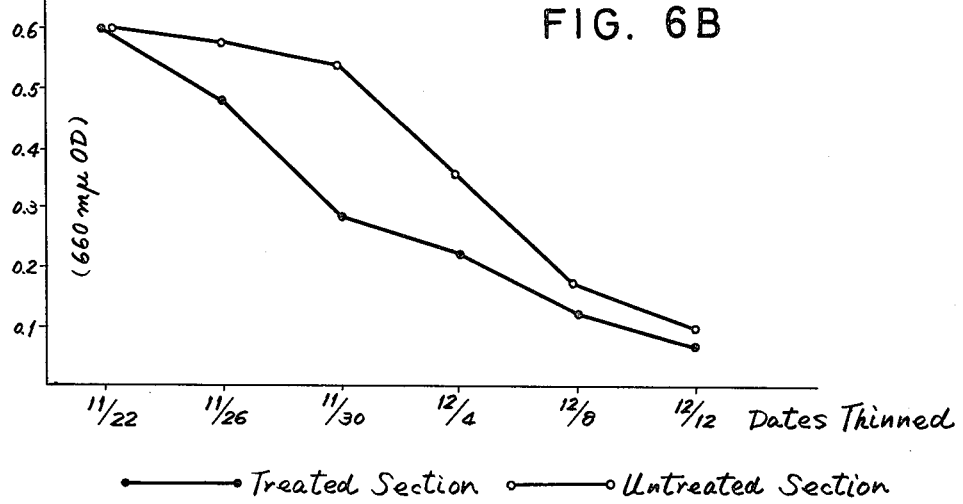

FIGS. 6A and 6B are graphs showing secular changes of the pigment in the pericarp of mandarin oranges in experiment 5.

DETAILED DESCRIPTION OF THE INVENTION

In this invention, the mycelium of edible fungus belonging to the genus Basidiomucetes are cultured by means of a culture medium or culture solution and cytoplasm obtained from metabolite and autolysis of the mycelium. Although Shiitake (*Lentinus edodes*), Hiratake (*Pleurotus ostreatus*), Nameko (*Ploliata nameko*), Enokitake (*Flammulina Velutipes* sing), Shimeji (*Lyophyllum aggregatum*), Kawaratake (*Coriolus Versicolor*), Sarunokoshikake (*Rigiooporus ulmarius*) and etc. may be used as the Basidiomycetes in this invention, the most active and superior was that extracted from Shiitake mycelium.

The culture medium employed may be either solid or liquid type culture mediums. The bagasse culture medium (culture medium composed of beet lees 12: rice bran 1), or sawdust culture medium (culture medium composed of sawdust 3: rice bran 1) which is normally used for growing fungus may be used for the former. Of these, as bagasse had no definite usage, it was principally disposed of by incineration in the past. However, it was easily and cheaply procured and was therefore advantageous cost-wise. On the other hand, GPY culture medium (liquid culture medium composed of a mixture of Glucose, Peptone and Yeast) and MY culture medium (liquid culture medium composed of a mixture of Malt extract powder and Yeast) may be considered for the latter. There is no particular change in the method of mycelium culture and the same methods as in the past can be used.

A feature of this invention is that mycelium and culture medium do not separate after mycelium of the genus Basidiomycetes is cultured in a solid or liquid culture medium. That is, metabolite of mycelium and the effective ingredients contained in mycelium were extracted from these mixtures of mycelium and culture mediums (hereafter called mycelium nutrient medium and tissue-medium) and results of separating and indentifying the extract confirmed that substances having cytokinin activity were contained as in the foregoing, and it was also determined that polysaccharide were also contained.

However, it may certainly be surmised that other effective ingredients are contained but they have still to be completely clarified. It is also still not clear as to the ingredients contained in the foregoing extracts that act to accelerate coloring and increase sweetness.

The water solvent employed in the extraction process is water or a water solution containing a small amount of water soluble organic solvent, acid and base. Methanol, ethanol or isopropylalcohol is principally used as the organic solvent. Hydrochloric acid, sulphuric acid or acetic acid may be used for the acid and ammonia, caustic soda, caustic potash, and sodium carbonate may be used for the base. However, water was principally used in this invention.

In this invention as extracted fluids from mycelium nutrient medium and tissue-medium existing in the natural world are used as the effective ingredients, they are absolutely safe for humans and for the trees. Also, as they do not have any ill effects and also contribute to accelerating coloring and increasing sweetness, they are extremely effective and will certainly be highly welcomed by the farmers.

We shall now describe a few examples of applications of this invention.

EXAMPLE 1

A solid culture medium composed of a mixture of 90% bagasse, 5% rice bran and 5% nutrients such as bran is sterilized by the usual method and Shiitake are then inoculated into this medium. Upon completion of inoculation, it is transferred to an air conditioned culture room with a temperature of 18° C. to 20° C. and a relative humidity of 60% to commence culture of mycelium. The culture medium in which mycelium has spread is then transferred and left in the culture room. The culture medium is removed from the culture room at the point where the Shiitake seedlings commence to emerge from the surface of the culture medium and is then crushed into thumb-sized lumps by means of a pulverizer. The crushed culture medium is then placed in a tank with water in the ratio of 5 liters of fresh water to 600 grams of culture medium and is then agitated and mixed for 4 to 5 hours at a temperature of 40° C. to 130° C. The metabolite of the mycelium and the effective ingredients contained in the mycelium fluid will dissolve in the water.

The suspension fluid obtained in this manner is placed in a flannel filter bag and filtered under pressure. The filtered fluid is filtered again by means of a membrane filter to remove fungus and extract the fluid with the effective ingredients contained in the metabolite of mycelium and in the mycelium fluid. Further, as this will be considerably diluted with water in actual usage, in the foregoing example 5 liters of the extract obtained by extracting 600 grams of culture medium dissolved in 5 liters of water shall be used as the undiluted fluid. The powder contained 30 g of effective ingredients is obtained by freezing and drying the above basic undiluted fluid.

The extract in the foregoing manner was used in the following example.

EXPERIMENT 1

Tests on sweetish summer oranges

Test site: Amakusa, Kumamoto Pre.
Test method: The above extract diluted 100 times is sprayed over the leaves at the rate of 450 liters per 10a.
Spraying period: On Oct. 7 and 14, 1978

Survey in relation to changes in pigment

Samples of the fruit were picked after the elapse of a certain fixed number of days after spraying and measurements were made with a spectrophotometer of the yellow pigment consisting mainly of carotin and xanthophyll, and also the green pigment consisting mainly of chlorophyll.

Adjustment of the Sample

Figure 1A:
FIGS. 1A and 1B are graphs showing secular changes of the pigment in the pericarp of sweetish summer oranges (Citrus Natsudaidai) in experiment 1.
Figure 1B:
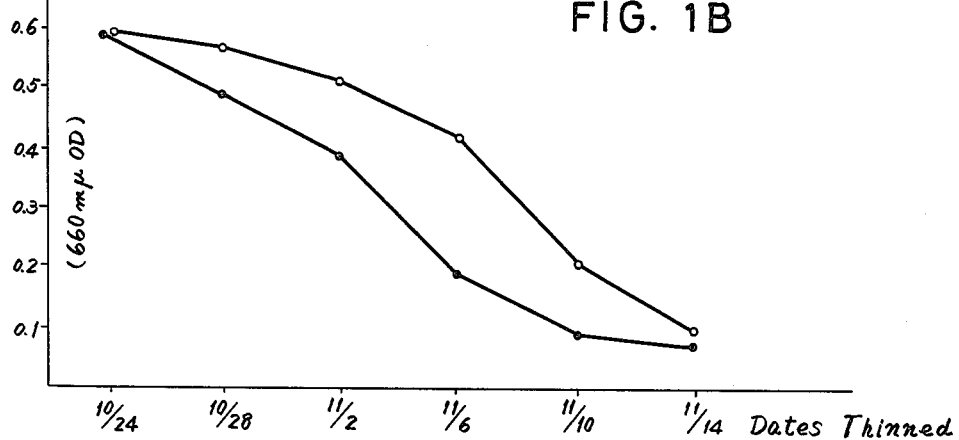

25 Grams of the pericarp is crushed in a mortar with quartz sand and 50 ml of acetone and centrifugation carried out. Extraction is repeated by adding acetone to the residue and repeating the process. After extracting all of the pigment, the extract is transferred to a separating funnel after reduced pressure compression and saponification to 100 ml. Add 50 ml of petroleum ether and 50 ml of water and shake. It will then separate into a yellowish layer of petroleum ether and a greenish layer of water. Light absorption is then measured of a 445 m$\mu$ layer of petroleum ether and a 660 m$\mu$ layer of water. Test results are as shown in FIGS. 1A and 1B. As in the foregoing, it was noted that there was a decrease in the green pigments while, on the other hand, there was an increase in the yellow pigment resulting from this treatment which clearly confirmed that this agent was effective in accelerating coloring.

| | Analysis results of ripe fruit (fruit juice). | | |
|---|---|---|---|
| Section | Item Sugar (%) | Citric Acid (%) | Soluble Solids (%) |
| Treated Section | 11.8 | 1.95 | 12.5 |
| Untreated Section | 9.6 | 1.92 | 11.5 |

As is clear from the analysis results, the sugar contents in the treated section is approximately 23% higher than that for the untreated section and clearly testifies to the fact that sugar content has increased.

EXPERIMENT 2

Tests on mandarin oranges

Test site: Uto, Kumamoto Pre.
Test method: The above extract diluted 100 times and sprayed over the leaves at the ratio of 450 liters per 10a.
Spraying period: Nov. 2 and 8, 1978

Survey in relation to chages in the pigment

The survey method and the adjustment method of samples used were the same as those used in the previous experiment.

Test results are as shown in FIGS. 2A and 2B.

As in the foregoing, it was noted that the green pigments decreased and the yellow pigments increased sharply as a results of this treatment.

| | Analysis results of ripe fruits (fruit juice) | | |
|---|---|---|---|
| Section | Item Sugar (%) | Citric Acid (%) | Soluble Solids (%) |
| Treated Section | 14.0 | 0.92 | 14.8 |
| Untreated Section | 11.0 | 0.74 | 12.4 |

As is clear from the above analysis results, sugar content has increased approximately 26% as compared to the untreated section. This clearly testifies to the fact that sugar content has increased.

EXPERIMENT 3

In view of test results such as in the above, the inventors have entrusted additional tests of this extract with the Kumamoto Pre. Experimental Fruit Laboratory.

Data of the experiments conducted are as follows.

Purpose of the tests: To confirm the effects of spraying Shiitake mycelium extract on accelerating coloring and increasing sugar content of citrus fruits.

Test supervisor: Kumamoto Pre. Experimental Fruit Laboratory

Sample trees: 6 year old Aoshima Mandarin Orange trees

Sample agent: Shiitake mycelium extract

Spraying density, spraying period and number of times.

| Spray Agent | Spraying Density | Spraying Period |
|---|---|---|
| Extract | 100 times | Nov. 2, Nov. 11, 1978 |
| Extract | 500 times | Nov. 4, Nov. 11, 1978 |
| Extract | 1000 times | Nov. 4, Nov. 11, 1978 |

Test Results (Particularly in relation to fruit quality)

| | | a | b | c | d | e | f |
|---|---|---|---|---|---|---|---|
| Dec.1 | A | 69.7 | 79.1 | 12.4 | 13.86 | 1.193 | 11.62 |
| | B | 68.6 | 74.9 | 10.2 | 11.17 | 0.952 | 11.73 |
| | C | 69.2 | 75.9 | 10.6 | 12.00 | 0.973 | 12.33 |
| | D | 69.4 | 78.1 | 10.3 | 11.58 | 0.970 | 11.94 |
| Dec.22 | A | 70.3 | 81.2 | 12.6 | 13.77 | 1.111 | 12.39 |
| | B | 71.5 | 76.5 | 10.0 | 11.28 | 0.909 | 12.41 |
| | C | 70.8 | 76.8 | 10.1 | 11.31 | 0.967 | 11.70 |
| | D | 69.5 | 75.2 | 10.1 | 11.28 | 0.955 | 11.81 |
| Feb.22 | A | 71.4 | 75.3 | 13.8 | 15.03 | 0.939 | 16.01 |
| | B | 71.4 | 73.0 | 11.0 | 12.37 | 0.757 | 16.34 |
| | C | 71.2 | 75.2 | 11.7 | 12.74 | 0.858 | 14.85 |
| | D | 71.2 | 76.0 | 10.5 | 11.31 | 0.760 | 14.88 |
| Mar.6 | A | 71.4 | 70.8 | 14.0 | 14.81 | 0.915 | 16.18 |
| | B | 69.6 | 74.1 | 11.3 | 12.64 | 0.729 | 17.34 |
| | C | 70.1 | 71.9 | 11.2 | 12.61 | 0.851 | 14.82 |
| | D | 69.2 | 74.7 | 11.1 | 12.37 | 0.739 | 16.74 |
| Apr.6 | A | 72.2 | 72.1 | 13.5 | 14.98 | 0.922 | 16.25 |
| | B | 66.2 | 75.4 | 11.6 | 12.64 | 0.694 | 18.22 |
| | C | 69.8 | 78.3 | 11.7 | 12.93 | 0.691 | 18.72 |
| | D | 68.6 | 78.3 | 11.3 | 12.61 | 0.682 | 18.50 |

A Extract diluted 100 times, 2 spraying
B Extract diluted 500 times, 2 spraying
C Extract diluted 1,000 times, 2 spraying
D Not sprayed
a Percentage of sarcocarp
b Percentage of fruit juice
c Indication of sugar
d Soluble solids
e Citric Acid
f Sweetness ratio FIGS. 3A to 3C and FIGS. 4A to 4C are graphs showing comparisons between sections sprayed with extract diluted 100 times and sections unsprayed particularly in relation to the amount of sugar and citric acid contained from the above analysis results.

SUMMARY OF TEST RESULTS (a) Sugar clearly showed a high degree of change in the 100 times section. Although transitions in sugar were high in the 500 times and 1,000 times section, they were lower than that compared to the 100 times section.

(b) The citric acid content was high in the 100 times and 1,000 times 2 sprayings section as compared to the unsprayed section. The transition was particularly high in the 100 times section as compared to the unsprayed section.

(c) Coloring in the 100 times section clearly showed advancement from mid-November.

(d) The above results clearly revealed the tendency for both sugar and citric acid to increase in density by spraying with high density sprays of the extract.

EXAMPLE 2

Place GPY (Glucose-Peptone-Yiest medium) culture medium in a container and place the container in an autoclave for 30 minutes at 121° C. to reduce bacteria. On one hand, the Shiitake seeds are picked up with a platinum roop and planted in the aforementioned culture medium. It is then placed in a culture room at 20° C. and, after shaking for a period of 1 minute at 120 times per minute, it is allowed to culture through its inner portion for a period of 7 to 8 days. The fungi will then spread throughout the culture medium and will gradually take ship to indicate that the fungus were grown sufficiently.

Add 1 liter of water to 1 liter of the fungus culture obtained by the above culture process, homogenize, and obtain the extract by filtering the resulting suspension fluid. After a suitable period of time, filtration concentration is carried out on the extract by means of an ultra-filtration film to obtain fluid extract again and this is further freeze-dried to obtain a brownish powder. Further, the amount of powder obtainable is 10 grams for each liter of extract.

Next, water was added to the forementioned powder and was used to carry out the following experiment.

EXPERIMENT 4

Tests on sweetish summer oranges

Test site: Amakusa, Kumamoto Pre.

Test method: 6 grams of the above powder was dissolved in 1,000 cc of water and this was sprayed over the leaves at the rate of 450 liters per 10a.

Spraying period: 15 and 22 October, 1978

Survey of changes in pigment

Survey method and adjustment method of the samples was the same as in the case of Application Example 1.

Figures 5A, 5B:
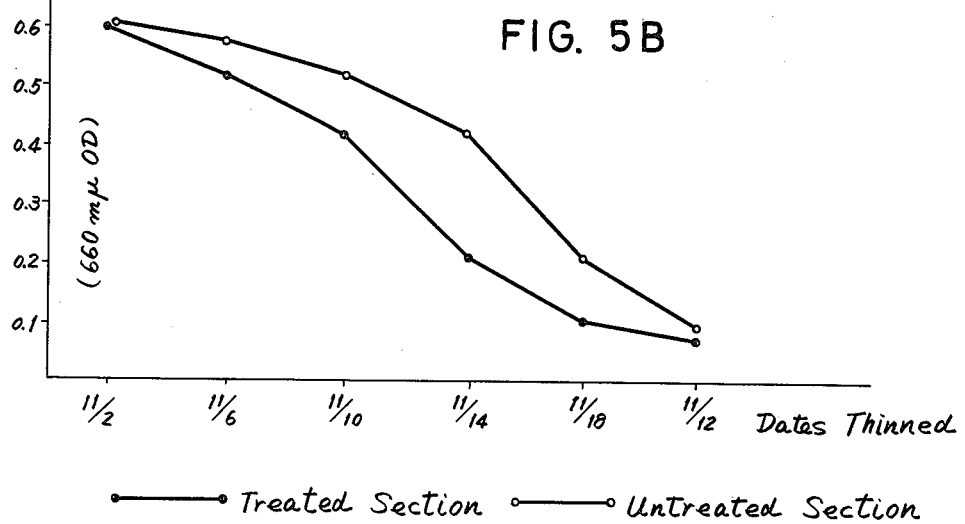

Test results were as shown in FIGS. 5A and 5B. As may be discerned, it was confirmed that the green pigment decreased and the yellow pigment increased as a result of this treatment.

| | Analysis results of ripe fruits (fruit juice). | | |
|---|---|---|---|
| Section | Item Sugar (%) | Citric Acid (%) | Soluble Solids (%) |
| Treated Section | 11.6 | 1.93 | 12.3 |
| Untreated Section | 9.6 | 1.92 | 11.5 |

As is clear from the above analysis results, sugar content in the treated section has increased approximately 20% in comparison with the untreated section. It was clearly confirmed that the sugar content had increased.

EXAMPLE 3

After culturing Enokitake mycelium by the same means as in Example 1, fluid extracts containing effective ingredients of mycelium culture was also obtained by the same procedure. Next, this fluid extract was employed to carry out the following experiment.

EXPERIMENT 5

Tests on mandarin oranges

Test site: Uto, Kumamoto Pre.

Test method: The above extract diluted 100 times was sprayed over the leaves at the rate of 450 liters per 10a.

Spraying period: 5 and 12 October, 1978

Survey in relation to changes in pigment

Survey method and adjustment method of the sample was the same as in Example 1.

Test results are as shown in FIGS. 6A and 6B.

As in the foregoing, it was confirmed that the green pigment decreased and the yellow pigments increased by means of this treatment. However, the coloring acceleration effect was slightly less than the extracts obtained from Shiitake mycelium culture.

| | Analysis results of ripe fruits (fruit juice). | | |
|---|---|---|---|
| Section | Item Sugar (%) | Citric Acid (%) | Soluble Solids (%) |
| Treated Section | 13.1 | 0.90 | 14.5 |
| Untreated Section | 11.1 | 0.74 | 12.4 |

As is clear from the above analysis results, the sugar content has increased approximately 18% compared to the untreated section and it has been confirmed that the amount of sugar content had increased. However, its accelerating effect on coloring and its effect on increasing sugar content was slightly less compared to that of the Shiitake mycelium extract.

Further, although the inventors carried out various experiments in relation to acceleration of coloring and increase in sugar content of myceliums of fungus other than the edible variety belonging to the foregoing Basidiomycetes such as shimeji, Nameko, Hiratake and Kawaratake and the results of the experiments were generally the same as in Example 4. In all cases they were inferior to that in the case of Shiitake myceliums.

We claim:

1. A method for accelerating the coloration and increasing the sugar content of citrus fruits which comprises applying to the citrus fruit plants a dilute, aqueous solution of the active ingredients obtained by water extraction of the mycelium nutrient medium and tissue medium of an edible fungus of the genus Basidiomycetes, concentrating, and subsequent aqueous dilution thereof to form said dilute, aqueous extract containing said active ingredients.

2. A method according to claim 1 for accelerating the coloration and increasing the sugar content of citrus fruits wherein the dilute, aqueous extract is obtained by diluting 100 times the extract obtained after adding 5 liters of water to 600 grams of solid culture medium.

3. A method according to claim 1 for accelerating the coloration and increasing sugar content of citrus fruits wherein the effective ingredients in the mycelium nutrient medium and tissue-medium are extracted by water.

4. A method according to claim 1 for accelerating the coloration and increasing sugar content of citrus fruits wherein the edible fungus belonging to the genus Basidiomycetes is selected from Shiitake, Hiratake, Nameko, Enokitake, Shimeji, Kawaratake and Sarunokoshikake.

* * * * *